(12) United States Patent
Saltis

(10) Patent No.: US 12,023,495 B2
(45) Date of Patent: Jul. 2, 2024

(54) METHOD AND APPARATUS FOR CONTROLLING PAIN

(71) Applicant: Lawrence M. Saltis, Akron, OH (US)

(72) Inventor: Lawrence M. Saltis, Akron, OH (US)

( * ) Notice: Subject to any disclaimer, the term of this patent is extended or adjusted under 35 U.S.C. 154(b) by 185 days.

(21) Appl. No.: 17/580,078

(22) Filed: Jan. 20, 2022

(65) Prior Publication Data
US 2022/0266008 A1  Aug. 25, 2022

Related U.S. Application Data

(60) Provisional application No. 63/152,969, filed on Feb. 24, 2021.

(51) Int. Cl.
*A61N 1/36*  (2006.01)
(52) U.S. Cl.
CPC ....... *A61N 1/3603* (2017.08); *A61N 1/36021* (2013.01)
(58) Field of Classification Search
CPC .......................... A61N 1/3603; A61N 1/36021
USPC .......................................................... 607/46
See application file for complete search history.

(56) References Cited

U.S. PATENT DOCUMENTS 4,456,012 A * 6/1984 Lattin .................... A61N 1/325
604/20

\* cited by examiner

*Primary Examiner* — Nadia A Mahmood
(74) *Attorney, Agent, or Firm* — Emerson, Thomson & Bennett, LLC; Roger D. Emerson

(57) ABSTRACT

A method and apparatus using high voltage and low amperage to control and reduce pain by applying an electrical stimulus to a patient. A generator module selectively generates a desired electrical stimulus to the patient via leads in electrical connection with the outputs of the generator module and connected to respective electrodes for attaching to at least one anatomical feature of a body of the patient, to administer the electrical stimulus. Duration, voltage and current circuits are included in the generator module for selectively establishing duration, voltage and current of the electrical stimulus. Respective duration, voltage and current slide switches manually adjust the respective duration, voltage and current circuits between a low level and a high level. A scale indicates the levels of duration, voltage and current such that low levels are indicated at a bottom of the scale and high levels are indicated at a top of the scale.

10 Claims, 5 Drawing Sheets

METHOD AND APPARATUS FOR CONTROLLING PAIN

This application claims the benefit of U.S. Provisional Application No. 63/152,969, entitled METHOD AND APPARATUS FOR CONTROLLING PAIN, filed Feb. 24, 2021, which is fully incorporated herein by reference.

I. BACKGROUND

A. Field of the Invention

This invention generally relates to methods and apparatuses related to controlling and reducing pain, and more specifically for controlling and reducing pain through electrical stimulation.

B. Description of Related Art

It is known to control or reduce pain through mechanical and electronic means. Complaints of pain are some of the more common and, many times, some of the more vexing symptom complaints with which a physician must deal when diagnosing and treating a patient's problems. But after completing an assessment and arriving at a firm diagnosis, treatments can vary widely requiring great skill and training to properly provide the least risky and invasive of the many approaches available.

Many patients treated for pain respond to the variety of medical and surgical therapies available. However, many others deal with chronic problems, such as poor results with their medications not controlling their pain, or at times, problems caused by the medicines themselves, such as allergies, drug reactions and interactions, or even the well-known, serious difficulties related to opiate drugs such as dependency and addiction. In addition, infections of implantable apparatuses or poor placement of the implants can occur.

Electrical stimulation has been used in various modalities and using different approaches and locations, either implanted or externally applied. Results have been of variable success and certainly of inconsistent predictable efficacy.

What is needed is a more effective and reliable method and apparatus to control or reduce pain through mechanical and electronic means. This invention will provide numerous other advantages as will be readily understood by a person of skill in the art.

II. SUMMARY

According to some embodiments of this invention, a method and apparatus for using high voltage and low amperage currents can provide desirable control, mitigation and elimination of pain.

In an exemplary embodiment, an apparatus is disclosed for applying an electrical stimulus to a patient, including a generator module for selectively generating a desired electrical stimulus to the patient and having outputs. First and second leads are in electrical connection with the outputs of the generator module and further electrically connected to respective first and second electrodes for attaching to at least one anatomical feature of a body of the patient, to administer the electrical stimulus.

A duration circuit of the generator module selectively establishes a duration of the electrical stimulus. A duration slide switch manually adjusts the duration circuit between a low level and a high level. A voltage circuit of the generator module selectively establishes a voltage level of the electrical stimulus. A voltage slide switch manually adjusts the voltage circuit between a low level and a high level. A current circuit of the generator module selectively establishes a current level of the electrical stimulus. A current slide switch manually adjusts the current circuit between a low level and a high level. A scale indicates the levels of duration, voltage and current such that low levels are indicated at a bottom of the scale and high levels are indicated at a top of the scale.

In a further exemplary embodiment, the duration slide switch, voltage slide switch, and current slide switch can be potentiometers for varying current within respective circuits. The duration circuit can include a timer component to deactivate the apparatus after an end of a predetermined treatment cycle based on position of the duration slider. The voltage circuit can include an oscillator circuit that interacts with a four-stage multiplier circuit configured to selectively step up and step down the voltage level based on position of the voltage slider. The current circuit can include an operational amplifier configured to selectively increase and decrease the current based on position of the current slider.

In an additional exemplary embodiment, the apparatus can be a hand-held device received within a housing including a battery compartment for retaining a battery as a power supply.

In a further additional exemplary embodiment, a method of electrical stimulation, can include affixing first and second electrodes to respective first and second body portions of an associated patient. Low amperage, high voltage signals are applied to the electrodes. One or more of voltage level, current level and duration are manually selectively varying by the patient.

In a still further additional exemplary embodiment, the first and second body portions can be a waist and ankle of the patient, where the electrical stimulation is performed to treat leg pain caused by root compression. Alternatively, the first and second body portions comprise a toe and a dorsal foot of the patient, where the electrical stimulation is performed to treat foot pain caused by nerve impingement. Further alternatively, the first and second body portions comprise a toe and a dorsal foot of the patient, wherein the electrical stimulation is performed to treat foot pain caused by neuropathy.

In a yet still further additional exemplary embodiment, the current level can be selectively varied between 1-4 milliamps and the voltage level is selectively varied between 12,500-50,000 volts.

The present invention thereby enables user-selected control of electrical stimulus intensity and voltage.

The present invention also thereby enables user-selected control of electrical stimulus duration.

The present invention additionally thereby provides a more effective and reliable method and apparatus to control or reduce pain through mechanical and electronic means.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

IV. DETAILED DESCRIPTION

Figure 1:
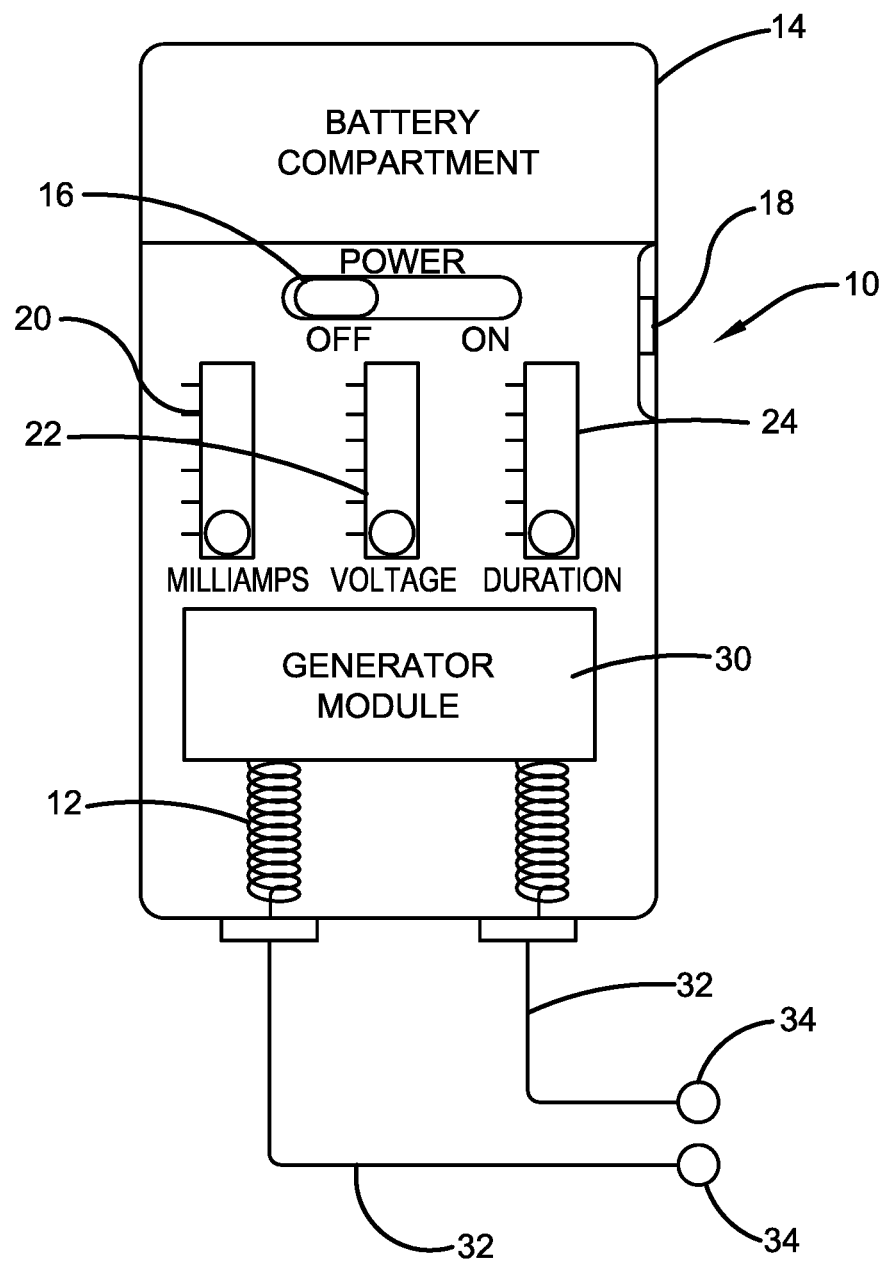
FIG. 1 is a front, perspective side view of an apparatus according to some embodiments of this invention.

Referring now to the drawings wherein the showings are for purposes of illustrating embodiments of the invention only and not for purposes of limiting the same, and wherein like reference numerals are understood to refer to like components, FIGS. 1-5 show an apparatus according to the invention.

Herein is described a novel non-invasive potential therapy and its delivery apparatus. The method and apparatus utilize controlled high-voltage and low-amperage electrical current stimulation. The inventive method and apparatus have generated favorable responses to intractable pain via a novel variety of electrical stimulation which has resulted in significant pain relief and control for patients.

As shown in FIG. 1, a current apparatus 10 is capable of generating electrical currents and signals that can be used to manage pain in a patient. The current apparatus 10 enables the patient to have operational control of the duration, current intensity, and voltage of the electrical signals.

With reference to FIG. 1, the apparatus 10 can be a hand-held device received within a housing 12 that can include a battery compartment 14 for retaining a battery as a power supply. Power is turned on and off using a power switch 16, as is commonly understood in the art. The housing 12 further includes an engagement button 18.

With continued reference to FIG. 1, the apparatus 10 includes slide switches that can be selectively varied by the patient to adjust the parameters of the electrical signal. The slide switches include a current slider 20, a voltage slider 22, and a duration slider 24. These slide switches 20, 22, 23 can be adjusted from between low levels at the bottom of a scale (as indicated in FIG. 1) and high levels at the top of the scale. Each of the slide switches 20, 22, 24 are potentiometers (variable resistors) for varying current within respective circuits (discussed hereinbelow). Each of the slide switches 20, 22, 24 are electrically connected to a generator module 30 which generates outputs to leads 32 that are electrically connected to respective electrodes 34, which are attached to the patient.

Figure 2:
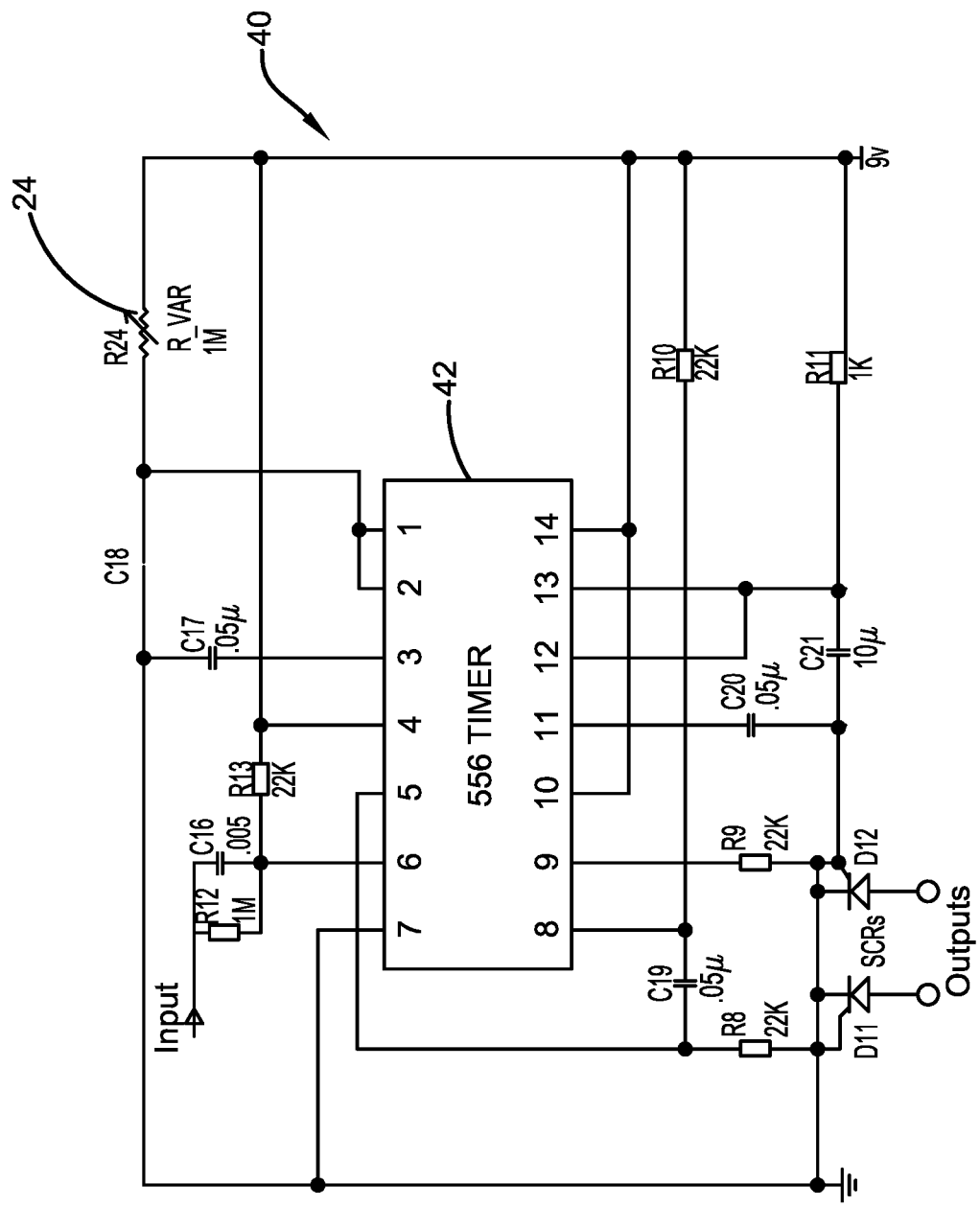
FIG. 2 is a schematic view of an electrical circuit used in the apparatus according to some embodiments of this invention.

With reference to FIG. 2, the generator module 30 includes a duration circuit 40 for establishing a duration of the electrical pain-relieving treatment. The duration circuit 40 is based on a timer component 42 and related circuitry to enable the device to be deactivated after the end of treatment cycle. The duration interval is established by the duration circuit 40 based on the position of the duration slider 24, such that a higher slider position on the scale results in a longer duration, and a lower slider position on the scale results in a shorter duration.

Figure 3:
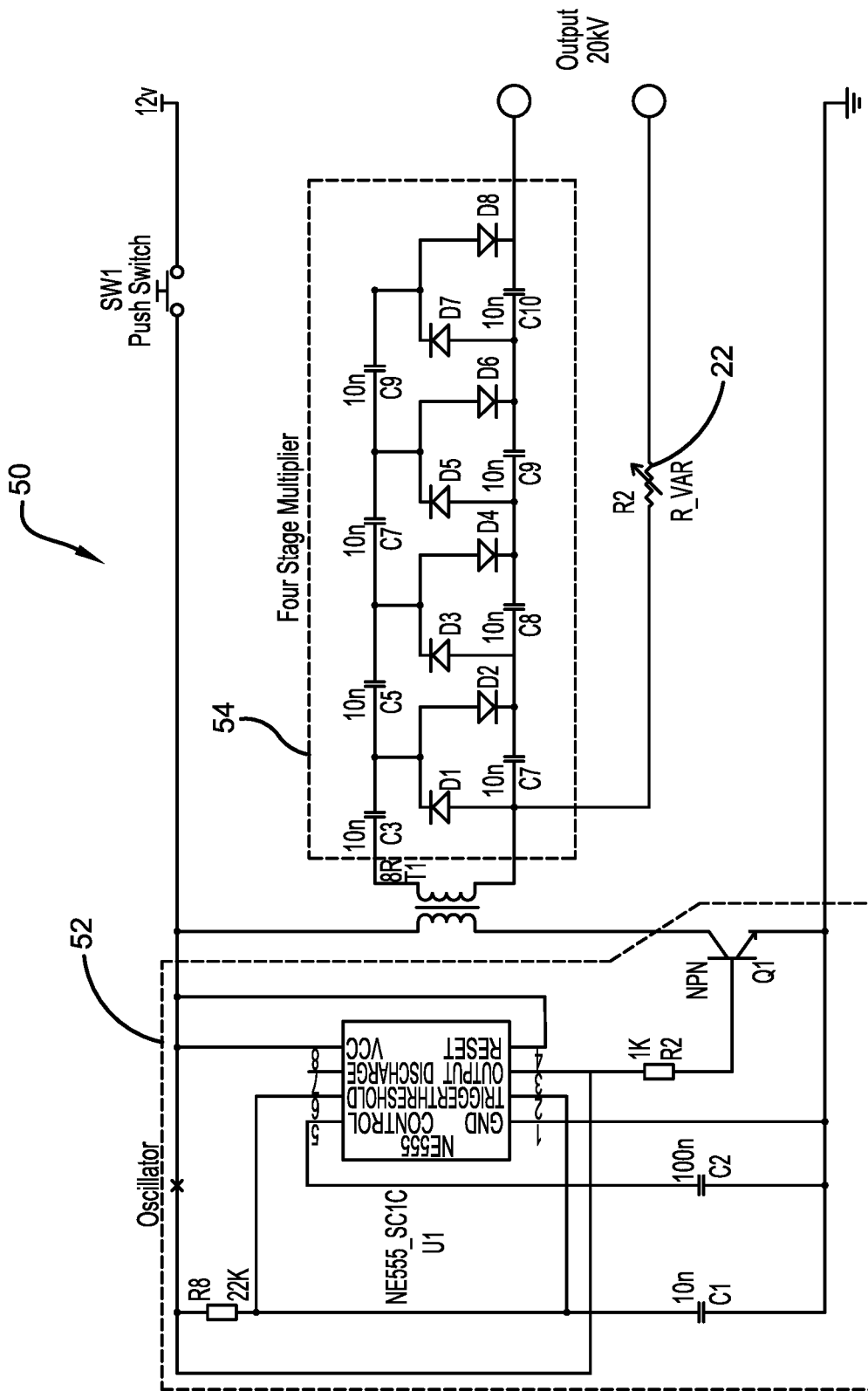
FIG. 3 is a schematic view of an electrical circuit used in the apparatus according to some embodiments of this invention.

With reference to FIG. 3, the generator module 30 also includes a voltage circuit 50 for establishing a desired voltage level of the electrical pain-relieving treatment. The voltage circuit 50 includes an oscillator circuit 52. The oscillator circuit 50 interacts with a four-stage multiplier circuit 54 which is configured to selectively step up and step down the voltage based on the position of the voltage slider 22, such that a higher slider position on the scale results in a higher voltage, and a lower slider position on the scale results in a lower voltage.

Figure 4:
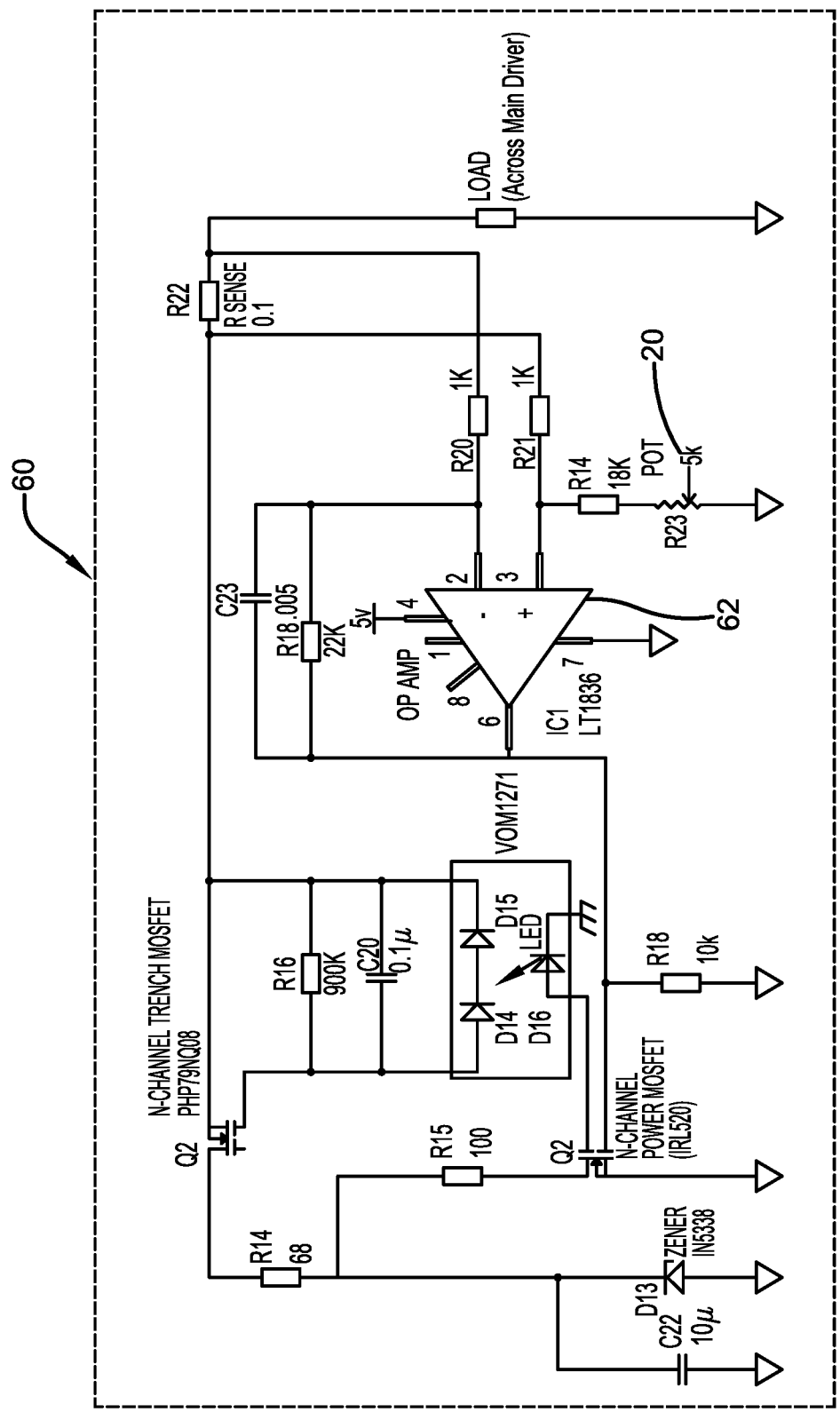
FIG. 4 is a schematic view of an electrical circuit used in the apparatus according to some embodiments of this invention.

With reference to FIG. 4, the generator module 30 also includes a current circuit 60 for establishing a desired current level of the electrical pain-relieving treatment. The current circuit 60 is based on an operational amplifier 62 which is configured to selectively increase and decrease the current based on the position of the current slider 20, such that a higher slider position on the scale results in a higher current, and a lower slider position on the scale results in a lower current.

Figure 5:
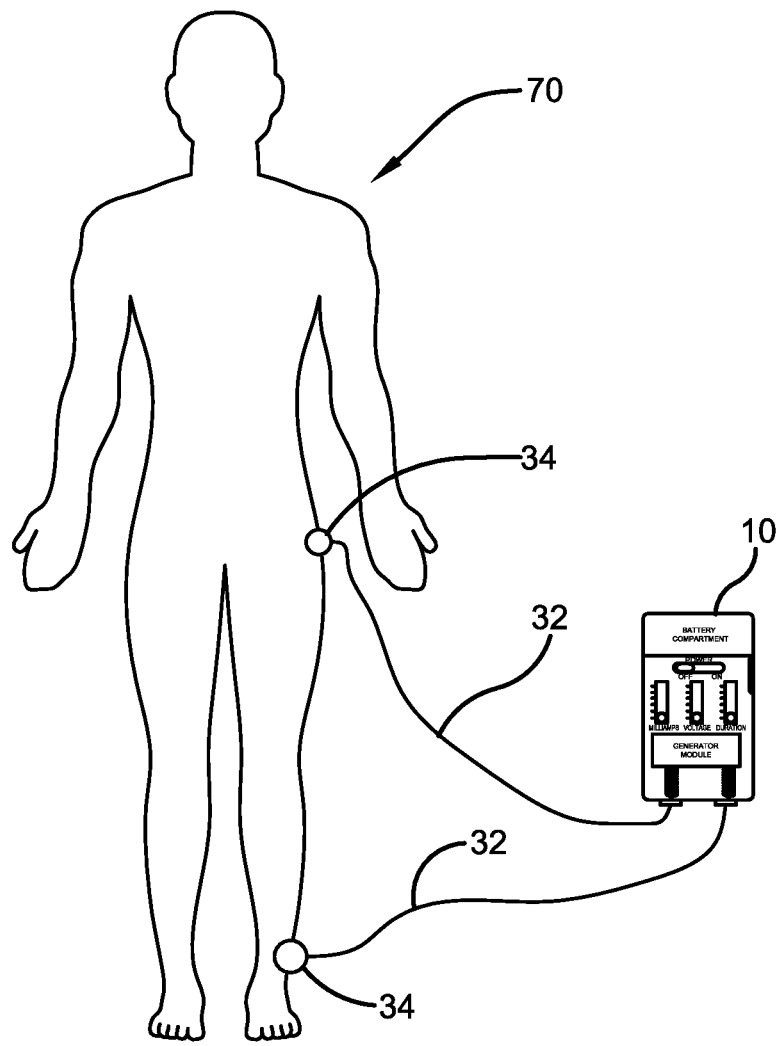
FIG. 5 is a schematic, front view of an associated patient with electrodes attached between the associated patient and the apparatus according to some embodiments of this invention.

As shown in FIG. 5, the apparatus 10 can be selectively and conveniently attached to an associated patient with the wire leads 32 that connect to the body of the patient 70 with electrodes 34. By adjusting the slide switches 20, 22, 24 in the manner described above, the level of the parameters of electrical stimulation can be selectively varied by the patient 70 to obtain a desired level of comfort and pain relief. This convenience makes the patient more tolerant and accepting of this mode of therapy. This aspect is helpful, as sometimes the patient community has been resistant to or unwilling to undergo more classic therapies which are often more complicated and expensive, and sometimes have proven ineffective.

As shown in FIG. 5, the apparatus 10, is capable of controlled delivery of variable and extremely high voltage and lower amperage stimulation to an extremity. The apparatus' electrodes 34 will be attached to the associated patient 70 in a manner based on the diagnosis and anatomy of the patient's medical problem and pain source.

The procedure aims at modulating chronic pain of various upper and lower extremity plexus lesions, root lesions, and various peripheral nerve lesions. Stimulus parameters determined and tolerated by the associated patient 70 and associated caregiver will direct delivery of pulses of controlled electrical wave forms which are designed to block spinal cord "gating mechanisms" of pain transmission through the nerve complexes and pathways theoretically through hyperpolarization of neuronal and interneuronal nerve pathways thus blocking the pain impulse transmission which usually eventually reaches the brain's pain perceptive areas.

Here are some exemplary treatments.

In one case, as depicted in FIG. 5, the associated patient complained of leg pain. The likely cause of the pain was root compression. Electrodes were placed at the waist and at the ankle. The apparatus was set to 1-4 milliamps and a voltage of 12,500-50,000 volts.

In another exemplary example, the associated patient complained of foot pain. The likely cause of the pain was nerve impingement. Electrodes were placed at the toes and at dorsal foot. The apparatus was set to 1-4 milliamps and a voltage of 12,000-50,000 volts.

In another exemplary example, the associated patient complained of foot pain. The likely cause of the pain was neuropathy. Electrodes were placed at the ankle and at the foot/toe. The apparatus was set to 1-4 milliamps and a voltage of 12,000-50,000 volts.

In light of the foregoing examples, it is believed that favorable results are obtainable when an electrical current of between 1 and 4 milliamps at a voltage of between 12,500 and 50,000 volts is delivered to specific parts of the body of an associated patient.

The apparatus 10 is rechargeable and easily portable as well as easy to store. One feature of one application of the apparatus 10 will likely be its utilization by an afflicted associated patient in their own home and at their convenience, whether day or night.

Numerous embodiments have been described herein. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof. Further, the "invention" as that term is used in this document is what is claimed in the claims of this document. The right to claim elements and/or sub-combinations that are disclosed herein as other inventions in other patent documents is hereby unconditionally reserve.

Having thus described the invention, it is now claimed:

1. An apparatus for applying an electrical stimulus to a patient, comprising:
    a generator module for selectively generating a desired electrical stimulus to the patient and having outputs;
    first and second leads in electrical connection with the outputs of the generator module and further electrically connected to respective first and second electrodes for attaching to at least one anatomical feature of a body of the patient, to administer the electrical stimulus;
    slide switches selectively varied by the patient to adjust parameters of the electrical stimulus;
    a duration circuit of the generator module for selectively establishing a duration of the electrical stimulus;
    wherein the slide switches comprise a duration slide switch for manually adjusting the duration circuit between a low level and a high level;
    a voltage circuit of the generator module for selectively establishing a voltage level of the electrical stimulus;
    wherein the slide switches further comprise a voltage slide switch for manually adjusting the voltage circuit between a low level and a high level;
    a current circuit of the generator module for selectively establishing a current level of the electrical stimulus;
    wherein the slide switches further comprise a current slide switch for manually adjusting the current circuit between a low level and a high level; and
    a scale for indicating the levels of duration, voltage and current such that low levels are indicated at a bottom of the scale and high levels are indicated at a top of the scale.

2. The apparatus of claim 1, wherein at least one of the duration slide switch, voltage slide switch, and current slide switch are potentiometers for varying current within respective circuits.

3. The apparatus of claim 1, wherein the duration circuit comprises a timer component to deactivate the apparatus after an end of a predetermined treatment cycle based on position of the duration slider.

4. The apparatus of claim 1, wherein the voltage circuit comprises an oscillator circuit that interacts with a four-stage multiplier circuit configured to selectively step up and step down the voltage level based on position of the voltage slider.

5. The apparatus of claim 1, wherein the current circuit comprises an operational amplifier configured to selectively increase and decrease the current based on position of the current slider.

6. The apparatus of claim 1, wherein the apparatus is a hand-held device received within a housing including a battery compartment for retaining a battery as a power supply.

7. A method of electrical stimulation, comprising:
    affixing first and second electrodes to respective first and second body portions of an associated patient;
    applying low amperage, high voltage signals to the electrodes; and
    manually selectively varying at least one of voltage level, current level and duration by the patient, wherein the current level is selectively varied between 1-4 milliamps and the voltage level is selectively varied between 12,500-50,000 volts.

8. The method of claim 7, wherein the first and second body portions comprise a waist and ankle of the patient, wherein the electrical stimulation is performed to treat leg pain caused by root compression.

9. The method of claim 7, wherein the first and second body portions comprise a toe and a dorsal foot of the patient, wherein the electrical stimulation is performed to treat foot pain caused by nerve impingement.

10. The method of claim 7, wherein the first and second body portions comprise a toe and a dorsal foot of the patient, wherein the electrical stimulation is performed to treat foot pain caused by neuropathy.

* * * * *